(12) United States Patent
Dugan

(10) Patent No.: US 8,075,451 B2
(45) Date of Patent: Dec. 13, 2011

(54) METHODS AND APPARATUS FOR MONITORING AND ENCOURAGING HEALTH AND FITNESS

(76) Inventor: Brian M. Dugan, Sleepy Hollow, NY (US)

( * ) Notice: Subject to any disclaimer, the term of this patent is extended or adjusted under 35 U.S.C. 154(b) by 0 days.

(21) Appl. No.: 12/979,275

(22) Filed: Dec. 27, 2010

(65) Prior Publication Data

US 2011/0091842 A1    Apr. 21, 2011

Related U.S. Application Data

(63) Continuation of application No. 11/676,666, filed on Feb. 20, 2007, now Pat. No. 7,857,730, which is a continuation of application No. 10/945,808, filed on Sep. 21, 2004, now Pat. No. 7,189,191, which is a continuation of application No. 09/702,179, filed on Oct. 30, 2000, now Pat. No. 6,811,516.

(60) Provisional application No. 60/162,502, filed on Oct. 29, 1999.

(51) Int. Cl.
*A63B 71/00* (2006.01)

(52) U.S. Cl. ............ 482/8; 482/1; 700/90; 705/26

(58) Field of Classification Search ........... 482/1–9, 482/900–902; 705/1, 15, 26, 28; 600/300; 700/90; 707/104.1
See application file for complete search history.

(56) References Cited

U.S. PATENT DOCUMENTS

| | | | |
|---|---|---|---|
| 3,717,857 A | 2/1973 | Evans |
| 3,788,647 A | 1/1974 | Evans |
| 3,815,427 A | 6/1974 | Gladstone |
| 3,834,702 A | 9/1974 | Bliss |
| 4,484,743 A | 11/1984 | Williams |
| 4,542,897 A | 9/1985 | Melton et al. |
| 4,735,410 A | 4/1988 | Nobuta |
| 4,817,938 A | 4/1989 | Nakao et al. |
| 4,858,930 A | 8/1989 | Sato |
| 4,976,435 A | 12/1990 | Shatford et al. |
| 5,001,632 A | 3/1991 | Hall-Tipping |
| 5,056,783 A | 10/1991 | Matcovich et al. |

(Continued)

FOREIGN PATENT DOCUMENTS

EP    0 753 836 A2    1/1997

(Continued)

OTHER PUBLICATIONS

Tom Foremski, Key Centre for Developing New Internet Devices, Financial Times, Survey London Edition 1 ED, p. 12, Oct. 2, 1996.

(Continued)

*Primary Examiner* — Glenn Richman
(74) *Attorney, Agent, or Firm* — Dugan & Dugan, PC

(57) ABSTRACT

Methods and apparatus are provided for monitoring and encouraging health and fitness. In accordance with a first aspect, an apparatus is provided that is adapted to assist in weight loss and exercise. The apparatus comprises a personal digital assistant (PDA) having computer program code adapted to assist in at least one of calorie counting, meal selection, meal suggestion, weight monitoring, weight loss or gain monitoring, fat consumption monitoring, sugar consumption monitoring and salt consumption monitoring. The PDA also includes computer program code adapted to display historical data regarding at least one of calorie counting, meal selection, meal suggestion, weight monitoring, weight loss or gain monitoring, fat consumption monitoring, sugar consumption monitoring and salt consumption monitoring. Numerous other embodiments are provided, as are methods, systems and computer program products.

19 Claims, 2 Drawing Sheets

U.S. PATENT DOCUMENTS

| | | | |
|---|---|---|---|
| 5,174,577 | A | 12/1992 | Warde et al. |
| 5,221,088 | A | 6/1993 | McTeigue et al. |
| 5,233,544 | A | 8/1993 | Kobayashi |
| 5,257,084 | A | 10/1993 | Marsh |
| 5,362,069 | A | 11/1994 | Hall-Tipping |
| 5,377,100 | A | 12/1994 | Pope et al. |
| 5,515,865 | A | 5/1996 | Scanlon |
| 5,527,239 | A | 6/1996 | Abbondanza |
| 5,591,104 | A | 1/1997 | Andrus et al. |
| 5,624,316 | A | 4/1997 | Roskowski et al. |
| 5,645,513 | A | 7/1997 | Haydocy et al. |
| 5,667,459 | A | 9/1997 | Su |
| 5,672,107 | A | 9/1997 | Clayman |
| 5,673,691 | A | 10/1997 | Abrams et al. |
| 5,688,183 | A | 11/1997 | Sabatino et al. |
| 5,694,340 | A | 12/1997 | Kim |
| 5,702,323 | A | 12/1997 | Poulton |
| 5,741,182 | A | 4/1998 | Lipps et al. |
| 5,781,698 | A | 7/1998 | Teller et al. |
| 5,884,281 | A | 3/1999 | Smith et al. |
| 5,885,156 | A | 3/1999 | Toyohara et al. |
| 5,911,635 | A | 6/1999 | Ogden |
| 5,918,603 | A | 7/1999 | Brown |
| 5,928,133 | A | 7/1999 | Halyak |
| 5,947,868 | A | 9/1999 | Dugan |
| 5,954,510 | A | 9/1999 | Merrill et al. |
| 6,024,675 | A | 2/2000 | Kashiwaguchi |
| 6,038,546 | A | 3/2000 | Ferro |
| 6,045,364 | A | 4/2000 | Dugan |
| 6,062,216 | A | 5/2000 | Corn |
| 6,152,856 | A | 11/2000 | Studor et al. |
| 6,173,610 | B1 | 1/2001 | Pace |
| 6,179,713 | B1 | 1/2001 | James et al. |
| D439,981 | S | 4/2001 | Kasabach et al. |
| 6,213,872 | B1 | 4/2001 | Harada et al. |
| 6,244,988 | B1 | 6/2001 | Delman |
| 6,251,010 | B1 | 6/2001 | Tajiri et al. |
| 6,261,102 | B1 | 7/2001 | Dugan et al. |
| 6,267,677 | B1 | 7/2001 | Tajiri et al. |
| 6,302,789 | B2 | 10/2001 | Harada et al. |
| D451,604 | S | 12/2001 | Kasabach et al. |
| 6,347,993 | B1 | 2/2002 | Kondo et al. |
| 6,354,940 | B1 | 3/2002 | Itou et al. |
| 6,375,572 | B1 | 4/2002 | Masuyama et al. |
| D460,971 | S | 7/2002 | Sica et al. |
| 6,456,749 | B1 | 9/2002 | Kasabach et al. |
| 6,478,736 | B1 | 11/2002 | Mault |
| 6,482,092 | B1 | 11/2002 | Tajiri et al. |
| 6,494,830 | B1 | 12/2002 | Wessel |
| 6,513,017 | B1 | 1/2003 | Howard et al. |
| 6,513,160 | B2 | 1/2003 | Dureau |
| 6,514,199 | B1 | 2/2003 | Alessandri |
| 6,527,711 | B1 | 3/2003 | Stivoric et al. |
| 6,553,386 | B1 | 4/2003 | Alabaster |
| 6,559,620 | B2 | 5/2003 | Zhou et al. |
| 6,595,858 | B1 | 7/2003 | Tajiri et al. |
| 6,595,929 | B2 | 7/2003 | Stivoric et al. |
| 6,605,038 | B1 | 8/2003 | Teller et al. |
| 6,628,847 | B1 | 9/2003 | Kasabach et al. |
| 6,641,482 | B2 | 11/2003 | Masuyama et al. |
| 6,652,383 | B1 | 11/2003 | Sonoda et al. |
| 6,705,972 | B1 | 3/2004 | Takano et al. |
| 6,720,983 | B1 | 4/2004 | Massaro et al. |
| 6,746,371 | B1 | 6/2004 | Brown et al. |
| 6,758,746 | B1 | 7/2004 | Hunter et al. |
| 6,786,825 | B2 | 9/2004 | Kawazu |
| 6,790,178 | B1 | 9/2004 | Mault et al. |
| 6,796,927 | B2 | 9/2004 | Toyama |
| 6,811,516 | B1 | 11/2004 | Dugan |
| 6,881,176 | B2 | 4/2005 | Oishi et al. |
| 6,888,779 | B2 | 5/2005 | Mollicone et al. |
| 6,902,513 | B1 | 6/2005 | McClure |
| 6,966,837 | B1 | 11/2005 | Best |
| 6,974,078 | B1 | 12/2005 | Simon |
| 7,020,508 | B2 | 3/2006 | Stivoric et al. |
| 7,021,140 | B2 | 4/2006 | Perkins |
| 7,041,049 | B1 | 5/2006 | Raniere |
| 7,068,860 | B2 | 6/2006 | Kasabach et al. |
| 7,153,262 | B2 | 12/2006 | Stivoric et al. |
| 7,189,191 | B2 | 3/2007 | Dugan |
| 7,261,690 | B2 | 8/2007 | Teller et al. |
| 7,285,090 | B2 | 10/2007 | Stivoric et al. |
| 2002/0022516 | A1 | 2/2002 | Forden |
| 2002/0082065 | A1 | 6/2002 | Fogel et al. |
| 2002/0082077 | A1 | 6/2002 | Johnson et al. |
| 2002/0090985 | A1 | 7/2002 | Tochner et al. |
| 2002/0107433 | A1 | 8/2002 | Mault |
| 2002/0160883 | A1 | 10/2002 | Dugan |
| 2003/0149344 | A1 | 8/2003 | Nizan |
| 2004/0023761 | A1 | 2/2004 | Emery |
| 2004/0053690 | A1 | 3/2004 | Fogel et al. |
| 2005/0032525 | A1 | 2/2005 | Gasbarro |
| 2005/0177051 | A1 | 8/2005 | Almen |
| 2005/0215340 | A1 | 9/2005 | Stites et al. |
| 2005/0288119 | A1 | 12/2005 | Wang et al. |
| 2006/0025229 | A1 | 2/2006 | Mahajan et al. |
| 2006/0025282 | A1 | 2/2006 | Redmann |
| 2006/0031102 | A1 | 2/2006 | Teller et al. |
| 2006/0122474 | A1 | 6/2006 | Teller et al. |
| 2006/0224051 | A1 | 10/2006 | Teller et al. |
| 2006/0264730 | A1 | 11/2006 | Stivoric et al. |
| 2007/0038038 | A1 | 2/2007 | Stivoric et al. |
| 2007/0109491 | A1 | 5/2007 | Howell et al. |
| 2007/0111811 | A1 | 5/2007 | Grober |
| 2007/0111858 | A1 | 5/2007 | Dugan |
| 2007/0135266 | A1* | 6/2007 | Dugan .............................. 482/8 |
| 2007/0167204 | A1 | 7/2007 | Lyle et al. |
| 2007/0197274 | A1 | 8/2007 | Dugan |
| 2007/0260482 | A1 | 11/2007 | Nurmela et al. |
| 2008/0027337 | A1 | 1/2008 | Dugan et al. |
| 2008/0085778 | A1 | 4/2008 | Dugan |
| 2009/0270743 | A1 | 10/2009 | Dugan et al. |
| 2010/0033303 | A1 | 2/2010 | Dugan et al. |
| 2010/0130298 | A1 | 5/2010 | Dugan et al. |

FOREIGN PATENT DOCUMENTS

| | | |
|---|---|---|
| EP | 1 292 217 B1 | 11/2005 |
| EP | 1 639 939 A1 | 3/2006 |
| EP | 1 292 218 B1 | 4/2006 |
| EP | 1 702 560 A1 | 9/2006 |
| EP | 1 743 571 A2 | 1/2007 |
| JP | 58044078 | 3/1983 |
| JP | 58 195577 | 11/1983 |
| JP | 58 195578 | 11/1983 |
| JP | 08103568 | 4/1996 |
| WO | WO 94/17860 | 8/1994 |
| WO | WO 96/05766 A1 | 2/1996 |
| WO | WO 97/02550 | 1/1997 |
| WO | WO 01/96986 A2 | 12/2001 |
| WO | WO 02/00111 A1 | 1/2002 |
| WO | WO 02/078538 A2 | 10/2002 |
| WO | WO 03/015005 A2 | 2/2003 |
| WO | WO 2004/019172 A2 | 3/2004 |
| WO | WO 2004/032715 A2 | 4/2004 |
| WO | WO 2004/034221 A2 | 4/2004 |
| WO | WO 2005/016124 A2 | 2/2005 |
| WO | WO 2005/027720 A2 | 3/2005 |
| WO | WO 2005/029242 A2 | 3/2005 |
| WO | WO 2005/092177 A1 | 10/2005 |

OTHER PUBLICATIONS

Busch, Fritz "Diabetes Institute Brings Dakota, New Ulm Together" Jun. 10, 2001. Ogden Newspapers, Inc.

Tibia.com website http://www.tibia.com!abouttibial?subtopic=whatistibia, Apr. 27, 2020.

"Bluetooth." Wikipedia: The Free Encyclopedia. Aug. 10, 2009 <http://en.wikipedia.org/wiki/Bluetooth>.

Notice of Allowance of U.S. Appl. No. 08/858,824 mailed Sep. 1, 1998.

Notice of Abandonment of U.S. Appl. No. 08/858,824 mailed Feb. 3, 1999.

Withdrawal of Notice of Allowance of U.S. Appl. No. 08/858,824 mailed May 11, 1999.

Notice of Allowance of U.S. Appl. No. 08/858,824 mailed Jul. 30, 1999.

Office Action of U.S. Appl. No. 09/104,917 mailed Sep. 22, 1998.
Dec. 22, 1998 Response to Office Action of U.S. Appl. No. 09/104,917 mailed Sep. 22, 1998.
Notice of Allowance of U.S. Appl. No. 09/104,917 mailed Mar. 15, 1999.
Office Action of U.S. Appl. No. 09/702,179 mailed Sep. 29, 2003.
Mar. 29, 2004 Response to Office Action of U.S. Appl. No. 09/702,179 mailed Sep. 29, 2003.
Notice of Allowance of U.S. Appl. No. 09/702,179 mailed Jun. 21, 2004.
Preliminary Amendment of U.S. Appl. No. 10/945,808 mailed Jul. 11, 2005.
Office Action of U.S. Appl. No. 10/945,808 mailed Apr. 14, 2006.
Sep. 14, 2006 Response to Office Action of U.S. Appl. No. 10/945,808 mailed Apr. 14, 2006.
Notice of Allowance of U.S. Appl. No. 10/945,808 mailed Nov. 3, 2006.
Preliminary Amendment of U.S. Appl. No. 10/094,396 mailed May 20, 2002.
Office Action of U.S. Appl. No. 10/094,396 mailed Oct. 4, 2004.
Mar. 4, 2005 Response to Office Action of U.S. Appl. No. 10/094,396 mailed Oct. 4, 2004.
Final Office Action of U.S. Appl. No. 10/094,396 mailed Jun. 2, 2005.
Nov. 2, 2005 Response to Final Office Action of U.S. Appl. No. 10/094,396 mailed Jun. 2, 2005.
Office Action of U.S. Appl. No. 10/094,396 mailed Feb. 9, 2006.
Aug. 9, 2006 Response to Office Action of U.S. Appl. No. 10/094,396 mailed Feb. 9, 2006.
Office Action of U.S. Appl. No. 10/094,396 mailed May 4, 2007.
Oct. 4, 2007 Response to Office Action of U.S. Appl. No. 10/094,396 mailed May 4, 2007.
Office Action of U.S. Appl. No. 10/094,396 mailed Jan. 25, 2008.
Jul. 25, 2008 Response to Office Action of U.S. Appl. No. 10/094,396 mailed Jan. 25, 2008.
Final Office Action of U.S. Appl. No. 10/094,396 mailed May 13, 2009.
Office Action of U.S. Appl. No. 11/692,185 mailed Oct. 7, 2009.
Notice of Non-Compliant Response of U.S. Appl. No. 11/768,167 mailed May 6, 2009.
Office Action of U.S. Appl. No. 11/768,167 mailed Aug. 19, 2009.
Office Action of U.S. Appl. No. 11/676,666 mailed Sep. 18, 2008.
Feb. 18, 2009 Response to Office Action of U.S. Appl. No. 11/676,666 mailed Sep. 18, 2008.
Office Action of U.S. Appl. No. 11/676,666 mailed Jun. 10, 2009.
Nov. 10, 2009 Response to Office Action of U.S. Appl. No. 11/676,666 mailed Jun. 10, 2009.
Office Action of U.S. Appl. No. 11/620,046 Mailed Nov. 12, 2009.
Office Action of U.S. Appl. No. 11/869,695 Mailed Nov. 17, 2009.
Dec. 21, 2009 Response to Office Action of U.S. Appl. No. 11/768,167 mailed Aug. 19, 2009.
Jan. 7, 2010 Response to Office Action of U.S. Appl. No. 11/692,185 mailed Oct. 7, 2009.
Feb. 12, 2010 Response to Office Action of U.S. Appl. No. 11/620,046 Mailed Nov. 12, 2009.
Final Office Action of U.S. Appl. No. 11/676,666 mailed Feb. 5, 2010.
Feb. 17, 2010 Response to Office Action of U.S. Appl. No. 11/869,695 Mailed Nov. 17, 2009.
Final Office Action of U.S. Appl. No. 11/692,185 mailed Mar. 3, 2010.
Final Office Action of U.S. Appl. No. 11/768,167 mailed Mar. 24, 2010.
Office Action of U.S. Appl. No. 10/094,396 mailed Apr. 14, 2010.
May 5, 2010 Response to Final Office Action of U.S. Appl. No. 11/676,666 mailed Feb. 5, 2010.
Final Office Action of U.S. Appl. No. 11/869,695 Mailed May 26, 2010.
Appeal Brief of U.S. Appl. No. 11/692,185 mailed Jun. 3, 2010.
Jun. 24, 2010 Response to Final Office Action of U.S. Appl. No. 11/768,167 mailed Mar. 24, 2010.
Final Office Action of U.S. Appl. No. 11/620,046 Mailed Jun. 23, 2010.
Advisory Action of U.S. Appl. No. 11/768,167 mailed Jun. 30, 2010.
Interview Summary of U.S. Appl. No. 11/676,666, filed Jul. 9, 2010.
Jul. 14, 2010 Response to Office Action of U.S. Appl. No. 10/094,396 mailed Apr. 14, 2010.
Advisory Action of U.S. Appl. No. 11/676,666 mailed Jul. 12, 2010.
Dugan et al., U.S. Appl. No. 12/839,098, filed Jul. 19, 2010.
Amendment submitted with RCE of U.S. Appl. No. 11/676,666, filed Aug. 5, 2010.
Examiner Interview Summary of U.S. Appl. No. 11/676,666 mailed Aug. 5, 2010.
Interview Summary of U.S. Appl. No. 11/676,666, filed Aug. 11, 2010.
Interview Summary of U.S. Appl. No. 11/869,695, filed Feb. 3, 2010.
Interview Summary of U.S. Appl. No. 11/869,695, filed Feb. 17, 2010.
Restriction Requirement of U.S. Appl. No. 10/945,808 mailed Aug. 22, 2005.
Sep. 22, 2005 Response to Restriction Requirement of U.S. Appl. No. 10/945,808 mailed Aug. 22, 2005.
Restriction Requirement of U.S. Appl. No. 10/945,808 mailed Jan. 10, 2006.
Feb. 10, 2006 Response to Restriction Requirement of U.S. Appl. No. 10/945,808 mailed Jan. 10, 2006.
Restriction Requirement of U.S. Appl. No. 10/094,396 mailed May 4, 2004.
Jul. 2, 2004 Response to Restriction Requirement of U.S. Appl. No. 10/094,396 mailed May 4, 2004.
Interview Summary of U.S. Appl. No. 10/094,396, filed Nov. 7, 2005.
Restriction Requirement of U.S. Appl. No. 10/094,396 mailed Oct. 31, 2006.
Jan. 31, 2007 Response to Restriction Requirement of U.S. Appl. No. 10/094,396 mailed Oct. 31, 2006.
Restriction Requirement of U.S. Appl. No. 11/620,046 Mailed Jun. 23, 2009.
Jul. 24, 2009 Response to Restriction Requirement of U.S. Appl. No. 11/620,046 Mailed Jun. 23, 2009.
Examiner Interview Summary of U.S. Appl. No. 11/692,185 mailed Jan. 15, 2010.
Interview Summary of U.S. Appl. No. 11/692,185, filed Jan. 26, 2010.
Interview Summary of U.S. Appl. No. 11/692,185, filed Feb. 3, 2010.
Notice of Allowance of U.S. Appl. No. 11/676,666 mailed Aug. 19, 2010.
Amendment After Final submitted with RCE of U.S. Appl. No. 11/869,695, filed Aug. 26, 2010.
Examiner Answer of U.S. Appl. No. 11/692,185 mailed Sep. 22, 2010.
Final Office Action of U.S. Appl. No. 10/094,396 mailed Oct. 14, 2010.
Office Action of U.S. Appl. No. 11/869,695 mailed Oct. 18, 2010.
Office Action of U.S. Appl. No. 11/768,167 mailed Dec. 27, 2010.
Notice of Abandonment of U.S. Appl. No. 11/620,046 Mailed Jan. 21, 2011.
Jun. 8, 2009 Response to Notice of Non-Compliant Response of U.S. Appl. No. 11/768,167 mailed May 6, 2009.
Mar. 18, 2011 Response to Office Action of U.S. Appl. No. 11/869,695 mailed Oct. 18, 2010.
Office Action of U.S. Appl. No. 12/696,040 mailed Jun. 8, 2011.
May 27, 2011 Response to Office Action of U.S. Appl. No. 11/768,167 mailed Dec. 27, 2010.
Final Office Action of U.S. Appl. No. 11/869,695 mailed Jun. 21, 2011.
Dugan, U.S. Appl. No. 13/183,405, filed Jul. 14, 2011.
Final Office Action of U.S. Appl. No. 11/768,167 mailed Aug. 19, 2011.

* cited by examiner

METHODS AND APPARATUS FOR MONITORING AND ENCOURAGING HEALTH AND FITNESS

This application is a continuation of and claims priority from U.S. patent application Ser. No. 11/676,666 filed Feb. 20, 2007, now U.S. Pat. No. 7,857,730, which is a continuation of and claims priority from U.S. patent application Ser. No. 10/945,808 filed Sep. 21, 2004, now U.S. Pat. No. 7,189,191, which is a continuation of and claims priority from U.S. patent application Ser. No. 09/702,179 filed Oct. 30, 2000, now U.S. Pat. No. 6,811,516, which claims priority from U.S. Provisional Patent Application Ser. No. 60/162,502, filed Oct. 29, 1999. All of the above applications are hereby incorporated by reference herein in their entirety.

FIELD OF THE INVENTION

The present application relates to methods and apparatus for monitoring and encouraging health and fitness.

BACKGROUND OF THE INVENTION

A fitness craze has recently swept the United States and many other countries. From fat-free potato chips to treadmills, people around the world have become obsessed with weight loss and healthy living. Accordingly, record numbers of new fitness products/exercise equipment have emerged to meet this obsession (including stair climbers, treadmills, recumbent bicycles, ski machines, and the like). However, no convenient mechanism has been developed for monitoring and encouraging health and fitness.

SUMMARY OF THE INVENTION

To overcome the needs of the prior art, methods and apparatus are provided for monitoring and encouraging health and fitness. In accordance with a first aspect of the invention, an apparatus is provided that is adapted to assist in weight loss and exercise. The apparatus comprises a personal digital assistant (PDA) having computer program code adapted to assist in at least one of calorie counting, meal selection, meal suggestion, weight monitoring, weight loss or gain monitoring, fat consumption monitoring, sugar consumption monitoring and salt consumption monitoring. The PDA also includes computer program code adapted to display historical data regarding at least one of calorie counting, meal selection, meal suggestion, weight monitoring, weight loss or gain monitoring, fat consumption monitoring, sugar consumption monitoring and salt consumption monitoring. Numerous other embodiments are provided, as are methods, systems and computer program products. Each computer program product may be carried by a medium readable by a computer (e.g., a carrier wave signal, a floppy disc, a hard drive, a random access memory, etc.).

Other objects, features and aspects of the present invention will become more fully apparent from the following detailed description of the preferred embodiments, the appended claims and the accompanying drawings.

DETAILED DESCRIPTION

Figure 1:
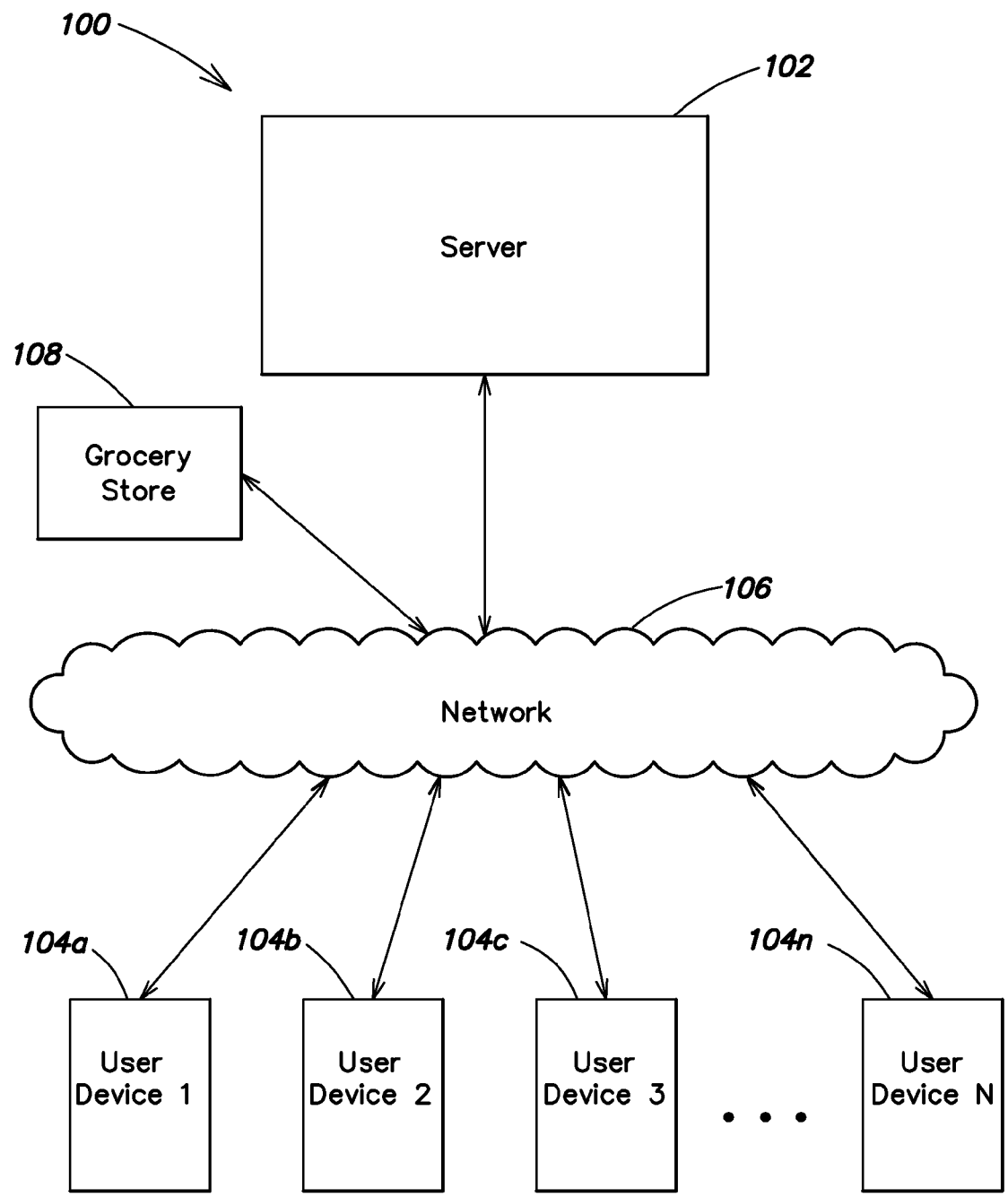
FIG. 1 is a schematic diagram of an exemplary system for monitoring and encouraging health and fitness.

FIG. 1 is a schematic diagram of an exemplary system 100 for monitoring and encouraging health and fitness. The system 100 includes a server 102 that may communicate with one or more user devices 104a-n via a network 106. As shown in FIG. 1, a grocery store 108 may also be in communication with the server 102 and/or with one or more of the user devices 104a-n via the network 106. Any other party such as a restaurant, a catering service, and/or any other relevant person or entity may be in communication with the server 102 in addition to, or in place of the grocery store 108. It will be understood that devices in communication need not be in continuous communication and actually may refrain from exchanging data/information most of the time. Additionally, devices may be in communication even though one or more steps must be performed before the devices may communicate (e.g., dialing a network service provider, connecting to a network service provider, logging onto a Web site, etc.).

The server 102 may comprise any conventional server (e.g., one or more conventional microprocessors) having computer program code contained therein as described below. Each user device 104a-n may comprise a desk top computer, a lap top computer, a set top box, a personal digital assistant (PDA), an internet-capable telephone device and/or any other device capable of communicating with the server 102 via the network 106, and each user device 104a-n may have computer program code contained therein as described below. The network 106 may comprise a local area network (LAN), a wide area network (WAN), the Internet, an intranet, an extranet or any other network. In general one or more of the user devices 104a-n, the grocery store 108, and/or any other relevant third party may communicate with the server 102 or amongst one another via any communications medium (e.g., via telephone, via facsimile, via mail, etc.).

As stated, the server 102 and/or one or more of the user devices 104a-n may contain computer program code adapted to direct the server 102 and/or the one or more user devices 104a-n in accordance with one or more embodiments of the invention.

Figure 2:
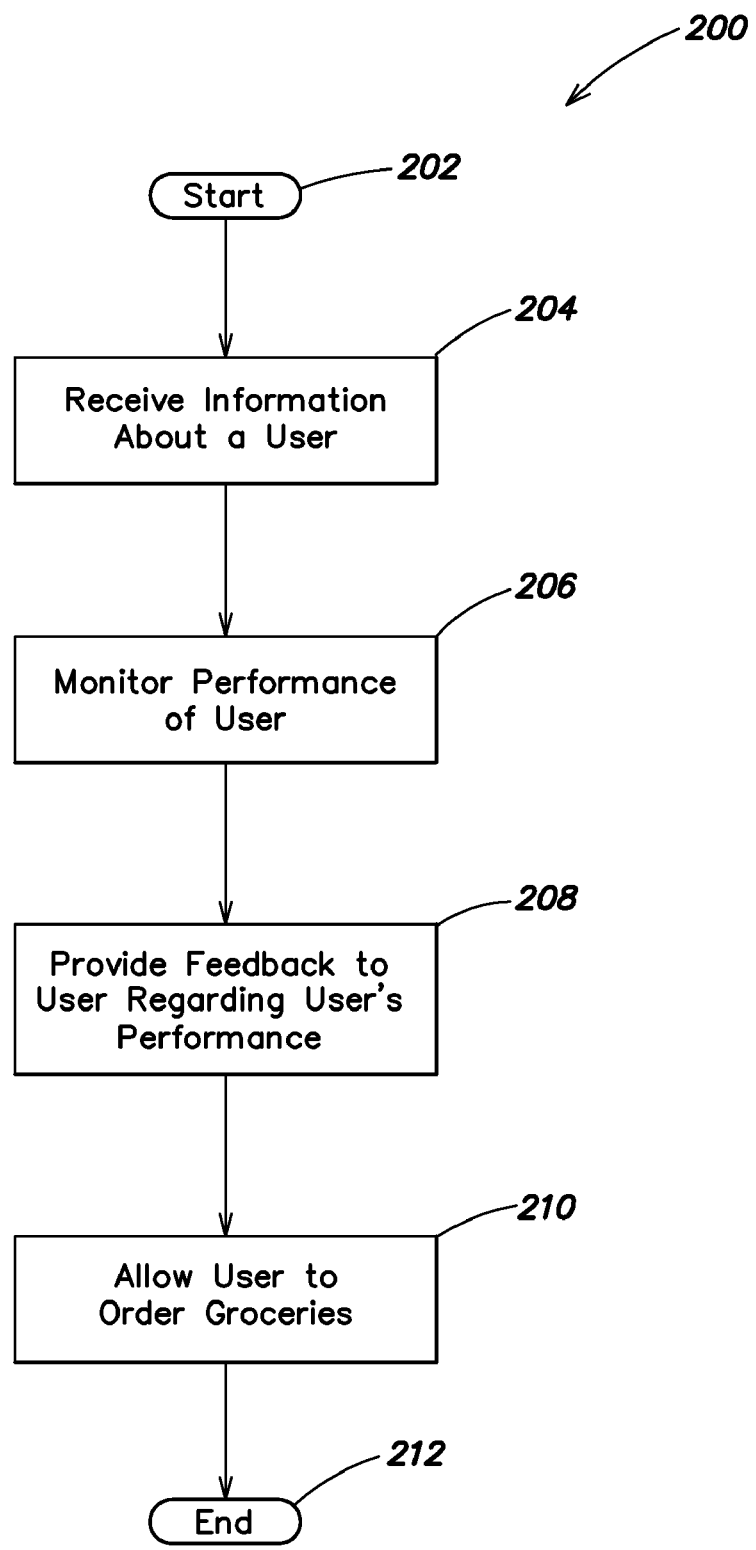
FIG. 2 is a flowchart of a first exemplary process of the system of FIG. 1.

FIG. 2 is a flowchart of a first exemplary process 200 of the system 100. With reference to FIG. 2, in step 202, the process 200 begins. In step 204, the server 102 receives information about a user. For example, if the server 102 is a Web server, the user may employ one of the user devices 104a-n to log-on to a Web site administered by the server 102, and to provide information to the server 102. Relevant information may include any type of demographic information (e.g., age, weight, height, sex, etc.), geographic/address information (e.g., where the user lives, contact information, etc.), goals or objectives of the user (e.g., weight loss, healthier diet, exercise objectives, etc.) or any other relevant information. In general, information about the user may be provided to the server 102 by any mechanism (e.g., via mail, via e-mail, via telephone, via cellular telephone, via facsimile, etc.). For example, information may be received via one or more HTTP transmissions or via some other communications protocol.

In step 206, the server 102 monitors the performance of the user (e.g., receives information from one or more of the user devices 104a-n about the user's food intake and/or exercise level and/or generates historical information about the user's performance). In step 208, the server 102 provides feedback to the user based on the monitored performance of the user (e.g., encouragement to exercise more, not to eat certain foods, to eat certain foods, etc.). The feedback may be provided at any time (e.g., periodically, randomly, etc.) and by any means (e.g., via mail, via e-mail, via facsimile, via telephone, etc.).

In step 210, the user (optionally) may employ one or more of the user devices 104a-n to order groceries from the grocery store 108 (e.g., in accordance with the dietary goals of the user). For example, the system 100 may be configured so as to:

- maintain on a PDA a list of grocery items purchased by a shopper;
- display on the PDA at least one of the grocery items within the maintained list of grocery items;
- allow selection of one or more of the displayed previously purchased grocery items;
- display at least one of the grocery items within the maintained a list of grocery items based on prior use patterns of the shopper;
- display a message that indicates that, based on prior use patterns of the shopper, at least one of the grocery items within the maintained list of grocery items should be purchased by the shopper;
- e-mail the shopper;
- display on a PDA a list of user-selectable grocery items;
- allow selection of at least one of the displayed selectable grocery items;
- display at least one characteristic of a selected grocery item (e.g., a characteristic selected from the group consisting of calories, fat content, salt content, cholesterol content, whether organically grown, whether low fat, whether suitable for diabetics, whether Kosher, price, size, shelf life and brand name);
- display a comparison of at least one characteristic of a plurality of selected grocery items;
- allow selection of the at least one characteristic.
- rank a plurality of selected grocery items based on the at least one characteristic.
- maintain on a PDA a list of grocery items purchased by a shopper;
- generate a report based on the list of purchased grocery items;
- generate a report selected from the group consisting of calorie consumption, fat consumption, sugar consumption, salt consumption and grocery cost;
- e-mail a report;
- generate a report periodically;
- display on a PDA a list of prepared foods;
- allow selection of at least one prepared food;
- display a recipe for each selected prepared food;
- display at least one user-selectable grocery item that is an ingredient of the recipe;
- display the cost of preparing each selected prepared food based on the cost of user-selected ingredients.
- display at least one user-selectable ingredient for the recipe based on a maintained list of grocery items purchased by a shopper;
- display a date when each user-selected ingredient was previously purchased by the shopper; and/or
- provide a link to a food preparation WEB site capable of generating a price quotation for the preparation of at least one selected prepared food.

In step 212, the process 200 ends.

The foregoing description discloses only exemplary embodiments of the invention, modifications of the above disclosed apparatus and method which fall within the scope of the invention will be readily apparent to those of ordinary skill in the art. For instance, in at least one embodiment of the invention, one or more of the user devices 104a-n is a personal digital assistant (PDA) having an application (e.g., computer program code) adapted to assist in calorie counting (e.g., keeping track of caloric intake), meal selection, meal suggestion, weight monitoring (e.g., via user entry or via a download from an electronic scale), weight loss or gain monitoring, fat consumption monitoring, sugar consumption monitoring and salt consumption monitoring. The one or more PDAs may include computer program code adapted to display historical data regarding at least one of calorie counting, meal selection, meal suggestion, weight monitoring, weight loss or gain monitoring, fat consumption monitoring, sugar consumption monitoring and salt consumption monitoring.

Exercise suggestions, exercise statistics (e.g., time exercised, distance run, type of exercise performed, historical data, etc.) may be stored/accessed via one or more of the user devices 104a-n. The information may be stored locally (e.g., within the PDA) or remotely (e.g., within the server 102). Additionally, a pulse monitor or other monitor may be provided that interfaces the PDA (e.g., by modifying the PDA if necessary to allow such an interface) and that automatically provides exercise information and/or calories-burned information to the PDA. A comparison of calorie intake versus calories burned may be automatically generated at any time (e.g., after a meal, at the end of the day, after exercise, etc.). Inspirational messages may be displayed (e.g., during exercise, prior to meal time, automatically if desired, etc.) to help with weight loss/exercise performance. Each PDA may be provided with a video game such as described in U.S. Pat. No. 5,947,868 (which is hereby incorporated by reference in its entirety) to further inspire exercise.

Each PDA may store, for example, grocery lists and may download information from a WEB site regarding suitable meals, products, etc., that are consistent with a user's diet and exercise goals. The WEB site may include a health food line such as WEIGHT WATCHER'S™, or any of the other grocery concepts described herein.

Accordingly, while the present invention has been disclosed in connection with the preferred embodiments thereof, it should be understood that other embodiments may fall within the spirit and scope of the invention, as defined by the following claims.

What is claimed is:

1. A method, comprising:
    employing a PDA to monitor exercise level information of a user;
    employing the PDA to communicate the exercise level information to a WEB server;
    employing the PDA to communicate geographic information about the user to the WEB server;
    employing the PDA to retrieve food information consistent with achieving a diet or exercise goal of the user by communicating with the WEB server, the food information including a list of prepared foods; and
    displaying the food information on the PDA.

2. The method of claim 1 further comprising employing the PDA to communicate food intake information to the WEB server.

3. The method of claim 2 further comprising employing the PDA to monitor food intake information of the user.

4. The method of claim 1 further comprising employing the PDA to receive weight information about the user.

5. The method of claim 4 wherein the weight information is communicated from an electronic scale.

6. The method of claim 1 wherein the retrieved food information is based on the monitored exercise level information.

7. The method of claim 1 wherein employing a PDA to monitor exercise level information of a user comprises employing the PDA to monitor a pulse of the user.

8. The method of claim 1 wherein employing a PDA to monitor exercise level information of a user comprises employing the PDA to monitor calories burned by the user.

9. The method of claim 1 wherein the food information comprises ingredient information.

10. The method of claim 1 further comprising displaying on the PDA a cost of a prepared food.

11. The method of claim 1 wherein the WEB server is in communication with a restaurant.

12. The method of claim 1 wherein the food information relates to a health food product line.

13. A method, comprising:
 employing a PDA to monitor food intake information of a user;
 employing the PDA to communicate the food intake information to a WEB server;
 employing the PDA to communicate geographic information about the user to the WEB server;
 employing the PDA to retrieve food information consistent with achieving a diet or exercise goal of the user by communicating with the WEB server, the food information including a list of prepared foods; and
 displaying the food information on the PDA.

14. The method of claim 13 further comprising employing the PDA to receive weight information about the user.

15. The method of claim 14 wherein the weight information is communicated from an electronic scale.

16. The method of claim 13 wherein the retrieved food information is based on the monitored food intake information.

17. The method of claim 13 further comprising displaying on the PDA a cost of a prepared food.

18. The method of claim 13 wherein the WEB server is in communication with a restaurant.

19. The method of claim 13 wherein the food information relates to a health food product line.

* * * * *